United States Patent [19]

Konya et al.

[11] Patent Number: 5,200,561
[45] Date of Patent: Apr. 6, 1993

[54] PROCESS FOR PRODUCING OPTICALLY ACTIVE AMINES

[75] Inventors: Naoto Konya, Takatsuki; Yukio Yoneyoshi, Misawa; Yoji Sakito, Takarazuka; Shinji Nishii, Ibaraki; Gohfu Suzukamo, Suita; Hiroko Sakane, Minoo, all of Japan

[73] Assignee: Sumitomo Chemical Company, Limited, Osaka, Japan

[21] Appl. No.: 771,569

[22] Filed: Oct. 7, 1991

[30] Foreign Application Priority Data

Oct. 8, 1990 [JP] Japan .................................. 2-271014

[51] Int. Cl.$^5$ .................. C07C 209/88; C07C 209/40
[52] U.S. Cl. .................... 564/373; 546/329; 558/354; 558/422; 564/302; 564/303; 564/304; 564/321; 564/374; 564/375; 564/382; 564/384; 564/385; 564/389; 564/415; 564/428; 564/429; 564/463; 564/489
[58] Field of Search .............. 564/302, 303, 304, 321, 564/373, 374, 375, 382, 384, 385, 389, 415, 428, 429, 463, 489; 546/329; 558/354, 422

[56] References Cited

FOREIGN PATENT DOCUMENTS 0237305 9/1987 European Pat. Off.
0311385 4/1989 European Pat. Off.

OTHER PUBLICATIONS

*Tetrahedron Letters*, vol. 29, No. 2, pp. 223-224, 1988, "Asymmetric Reduction of Oxime Ethers, Distinction of Anti and Syn Isomers Leading to Enantiomeric Amines", Sakito et al.
*J. Chem. Soc.*, Perkins Trans. 1, 1985, pp. 2039-2044, Itsuno et al., "Asymmetric Synthesis Using Chirally Modified Borohydrides. Part 3. Enantioselective Reduction of Ketones and Oxime Ethers with Reagents Prepared from Borane and Chiral Amino Alcohols".
Sakito et al. "Asymmetric Reduction, etc." vol. 29, No. 2, pp. 223-224 (1988).
Itsuno et al., "Asymmetric Synthesis using Ketones and Oxime Ethers, etc." *J. Chem Soc.* Perkins Trans. 1, 1985 pp. 2039-2044.
March *Advanced Organic Chemistry*, 3rd Ed, John Wiley and Sons New York, 1985, pp. 702-703.

*Primary Examiner*—Richard L. Raymond
*Assistant Examiner*—Peter G. O'Sullivan
*Attorney, Agent, or Firm*—Stevens, Davis, Miller & Mosher

[57] ABSTRACT

Disclosed is a process for producing an optically active amine represented by the formula (IV)

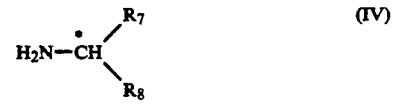

wherein $R_7$ and $R_8$ each denote an alkyl group, aryl group or aralkyl group, providing that they do not denote the same group at the same time, and * indicates an asymmetric carbon atom, which comprises reacting an asymmetric reducing agent obtained from (1) an optically active amine derivative represented by the formula (I)

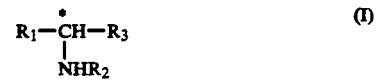

wherein $R_1$ denotes an alkyl group, aryl group or aralkyl group; $R_2$ denotes a hydrogen atom, alkyl group or aralkyl group; $R_3$ denotes an aryl group or a substituent represented by the formula (II)

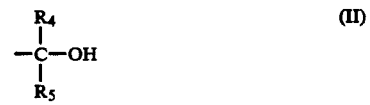

wherein $R_4$ and $R_5$ each denote a hydrogen atom, aryl group or aralkyl group, and * is as defined above, (2) a metal borohydride and (3) sulfuric acid, with either the syn-isomer or the anti-isomer of an oxime derivative represented by the formula (III) or with a mixture rich in either one of the two isomers

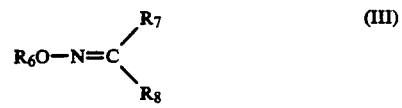

wherein $R_6$ denotes an alkyl group, aralkyl group or alkyl-substituted silyl group, and $R_7$ and $R_8$ are as defined above.

The optically active amine obtained can be used as a resolving agent for preparing medicinal agents, agricultural chemicals, or intermediates thereof.

22 Claims, No Drawings

PROCESS FOR PRODUCING OPTICALLY ACTIVE AMINES

BACKGROUND OF THE INVENTION

1. Field of the Invention

The present invention relates to a process for producing optically active amines. In more particular, it relates to a process for producing an optically active amine represented by the formula (IV)

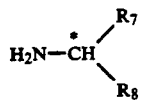
(IV)

wherein $R_7$ and $R_8$ each denote an alkyl group, aryl group or aralkyl group, providing that they do not denote the same group at the same time, and * indicates an asymmetric carbon atom.

2. Description of the Prior Art

The optically active amines represented by the formula (IV) are compounds important as resolving agents for preparing medicinal agents, agricultural chemicals, intermediates thereof, etc. It is already well known that they may be produced by first preparing a racemic compound and then resolving it by using an optically active acid or the like (cf., for example, Optical Resolution Procedures for Chemical Compounds, Vol. 1).

The prior method of producing an optically active amine by means of optical resolution comprises first preparing a racemic compound, then making an optically active acid or the like act thereon to form diastereomeric salts, crystallizing one of the diastereomeric salts thus formed by making use of the solubility difference of the diastereomeric salts, then separating the salt, thereafter reacting an alkali therewith to decompose the salt, and separating and recovering an optically active amine, one of the antipodes. Thus, the method has the disadvantages of complicated operations and poor efficiency.

The present inventors have made extensive study to solve the above-mentioned problems through a process using asymmetric synthesis. As a result, it was found and already proposed that an optically active amine can be prepared at a stretch by reacting an asymmetric reductant obtained from an optically active amine derivative and a boron hydride compound, with an oxime derivative and that an optically active amine of any desired absolute steric configuration can be prepared by proper use of either the anti-isomer or the syn-isomer of the oxime derivative [Japanese Patent Application KOKAI (Laid-Open) No. 63-99041; Tetrahedron Letters, 29, 223 (1988)].

Subsequently, the present inventors have made further study on a process that uses as the borohydride a metal borohydride which is easier to handle and less expensive. As the result, it has been found that by using a metal borohydride in combination with a specific mineral acid, the yield of the intended product can be improved and the amount of the metal borohydride to be used can be reduced. The present invention has been accomplished on the basis of the above finding along with further investigation.

SUMMARY OF THE INVENTION

According to the present invention, there is provided an industrially excellent process for producing an optically active amine represented by the formula (IV)

(IV)

wherein $R_7$ and $R_8$ each denote an alkyl group, aryl group or aralkyl group, providing that they do not denote the same group at the same time, and * indicates an asymmetric carbon atom, which comprises reacting an asymmetric reducing agent obtained from (1) an optically active amine derivative represented by the formula (I)

(I)

wherein $R_1$ denotes an alkyl group, aryl group, or aralkyl group; $R_2$ denotes a hydrogen atom, alkyl group or aralkyl group; $R_3$ denotes an aryl group or a substituent represented by the formula (II)

(II)

wherein $R_4$ and $R_5$ each denote a hydrogen group or aralkyl group; and * is as defined above, (2) a metal borohydride and (3) sulfuric acid, with either the syn-isomer or the anti-isomer of an oxime derivative represented by the formula (III) or with a mixture rich in either one of the two isomers

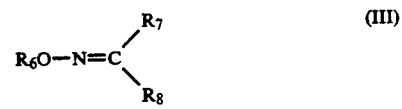
(III)

wherein $R_6$ denotes an alkyl group, aralkyl group or alkyl-substituted silyl group, and $R_7$ and $R_8$ are as defined above.

DETAILED DESCRIPTION OF THE INVENTION

The present invention will be described in detail below.

In the present invention, which is characterized by using an asymmetric reducing agent obtained from an optically active amine derivative, a metal borohydride and a specific mineral acid, i.e., sulfuric acid, the optically active amine derivative may be, for example, an optically active amine represented by the formula (I).

As examples of $R_1$ in the formula (I), there may be mentioned an alkyl group of 1-6 carbon atoms such as methyl, ethyl, propyl, butyl, pentyl, hexyl etc., a phenyl group, and an aralkyl group of 7-12 carbon atoms such as benzyl, phenylethyl, phenylpropyl, phenylbutyl, phenylpentyl, phenylhexyl, etc.

As examples of $R_2$, there may be mentioned a hydrogen atom and an alkyl group of 1-6 carbon atoms and an aralkyl group of 7–12 carbon atoms similar to those listed for $R_1$.

As examples of $R_4$ and $R_5$, when $R_3$ is a substituent of the formula (II), mention may be made of a hydrogen atom, a phenyl group, phenyl groups substituted with an alkyl of 1–6 carbon atoms such as methyl, ethyl, propyl, butyl, pentyl, hexyl, etc., phenyl groups substituted with an alkoxy of 1–6 carbon atoms such as methoxy, ethoxy, propoxy, butoxy, pentyloxy, hexyloxy, etc., phenyl groups substituted with said alkyl and alkoxy; an aralkyl group of 7–12 carbon atoms and an alkyl group of 1–6 carbon atoms similar to those mentioned for $R_1$.

Specific examples of the amine of the formula (I) include optically active norephedrine, ephedrine, 2-amino-1-(2-methylphenyl)-1-propanol, 2-amino-1-(2-ethylphenyl)-1-propanol, 2-amino-1-(2-methoxyphenyl)-1-propanol, 2-amino-1-(2-ethoxyphenyl)-1-propanol, 2-amino-1-(2,5-dimethylphenyl)-1-propanol, 2-amino-1-(2,5-diethylphenyl)-1-propanol, 2-amino-1-(2,5-dimethoxyphenyl)-1-propanol, 2-amino-1-(2,5-diethoxyphenyl)-1-propanol, 2-amino-1-(2-methoxy-5-methylphenyl)-1-propanol, 2-amino-1-phenyl-1-butanol, 2-amino-1-(2-methylphenyl)-1-butanol, 2-amino-1-(2-ethylphenyl)-1-butanol, 2-amino-1-phenyl-1-pentanol, 2-amino-1-(2,5-dimethoxyphenyl)-1-pentanol, 2-amino-1-phenyl-1-hexanol, 2-amino-1-phenyl-1-heptanol, 2-amino-1-phenyl-1-octanol, 2-amino-1,2-diphenylethanol, 2-amino-1-propanol, 2-amino-3-methyl-1-butanol, 2-amino-1-butanol, 2-amino-4-methyl-1-pentanol, 2-amino-3-methyl-1-pentanol, 2-amino-2-phenylethanol, 2-amino-3-phenyl-1-propanol, 2-amino-1,1-diphenyl-1-propanol, 2-amino-1,1-diphenyl-1-butanol, 2-amino-1,1-diphenyl-4-methyl-1-pentanol, 2-amino-1,1-diphenyl-3-methyl-1-pentanol, 2-amino-1,1-diphenyl-3-methyl-1-butanol, 2-amino-1,1,2-triphenylethanol, 2-amino-1,1,3-triphenyl-1-propanol, 2-amino-1,1-dibenzyl-1-propanol, 2-amino-1,1-di(2-methoxyphenyl)-4-methyl-1-pentanol, 2-amino-1,1,4-trimethyl-1-pentanol, 2-amino-1,1-dimethyl-4-methyl-1-pentanol, etc.

When $R_3$ is an aryl group, the aryl group may be, for example, phenyl; hydroxyphenyl groups optionally substituted with an alkyl of 1–6 carbon atoms or an alkoxy group of 1–6 carbon atoms such as 2-hydroxyphenyl, 2-hydroxy-3-methylphenyl, 2-hydroxy-3-ethylphenyl, 2-hydroxy-3-methoxyphenyl, 2-hydroxy-3-ethoxyphenyl, 2-hydroxy-5-methoxyphenyl, 2-hydroxy-5-ethoxyphenyl, 2-hydroxy-4-methylphenyl, 2-hydroxy-5-methylphenyl, 2-hydroxy-6-methylphenyl, 2-hydroxy-6-methoxyphenyl, etc.; 1-naphthyl, 2-naphthyl, and the like.

As specific example of the compound, there may be mentioned optically active 1-(2-hydroxyphenyl)ethylamine, 1-(2-hydroxy-3-methylphenyl)ethylamine, 1-(2-hydroxy-3-ethylphenyl)ethylamine, 1-(2-hydroxy-3-methoxyphenyl)ethylamine, 1-(2-hydroxy-3-ethoxyphenyl)ethylamine, 1-(2-hydroxy-5-methoxyphenyl)ethylamine, 1-(2-hydroxy-5-ethoxyphenyl)ethylamine, 1-(2-hydroxy-4-methylphenyl)ethylamine, 1-(2-hydroxy-5-methylphenyl)ethylamine, 1-(2-hydroxyphenyl)propylamine, 1-(2-hydroxy-3-ethylphenyl)propylamine, 1-(2-hydroxy-3-methoxyphenyl)propylamine, 1-(2-hydroxy-5-methoxyphenyl)propylamine, 1-(2-hydroxy-6-methylphenyl)ethylamine, 1-(2-hydroxy-3-ethylphenyl)ethylamine, 1-(2-hydroxy-6-methoxyphenyl)propylamine, 1-phenylethylamine, 1-(1-naphthyl)ethylamine, 1-(2-naphthyl)ethylamine, etc. Such optically active amine derivatives can be prepared, for example, by asymmetric reduction of the oxime derivative of corresponding ketone compounds (Japanese Patent Application KOKAI (Laid-Open) Nos. 02-238 and 02-289).

In the present invention, in which an asymmetric reducing agent obtained from an optically active amine derivative as listed above, a metal borohydride and sulfuric acid is used, the metal borohydride may be, for example, lithium borohydride, sodium borohydride, potassium borohydride, zinc borohydride, etc. Usually sodium borohydride is employed. The amount of the metal borohydride used is, in terms of borane, usually 0.8 to 8 moles, preferably about 1.5 to 5 moles, per mole of the optically active amine derivative.

The sulfuric acid used is preferably of high concentration. Although concentrated sulfuric acid is usually employed, it is also possible to make the reaction proceed more efficiently by using 100% sulfuric acid or such. The amount of sulfuric acid employed is usually 0.7 to 1.3 equivalents relative to the metal borohydride.

Preparation of the asymmetric reducing agent is usually conducted in the presence of a solvent. Examples of the solvent include ethers such as dioxane, tetrahydrofuran, diglyme, triglyme, etc.; sulfides such as dimethyl sulfide, diethyl sulfide, tetrahydrothiophene, etc.; the mixtures thereof; and the mixtures thereof with hydrocarbons such as benzene, toluene, xylene, chlorobenzene, chloroform, 1,2-dichloroethane, etc.

The asymmetric reducing agent is usually prepared by adding sulfuric acid to the mixture of solvent, optically active amine derivative, metal borohydride, etc. The temperature of preparation is usually 100° C. or below, preferably 0° C. to 80° C.

In the present invention, the asymmetric reducing agent thus obtained is reacted with either the syn-isomer or the anti-isomer of the oxime derivative represented by the formula (III) or with a mixture rich in either one of the two isomers. As examples of $R_6$ in said oxime derivative, there may be mentioned alkyl groups of 1–10 carbon atoms such as methyl, ethyl, propyl, butyl, pentyl, cyclopentyl, hexyl, cyclohexyl, heptyl, cycloheptyl, octyl, cyclooctyl, nonyl, decyl, etc , aralkyl groups of 7–12 carbon atoms such as benzyl, β-phenethyl, naphthyl, etc., and alkylsilyl groups of 3–12 carbon atoms such as trimethylsilyl, dimethyl-t-butylsilyl, tri-n-propylsilyl, tri-n-butylsilyl, etc.

As examples of the substituents $R_7$ and $R_8$, there may be mentioned phenyl, halogen-substituted phenyls such as o-, m- and p-chlorophenyl, o-, m- and p-bromophenyl, 2,3-, 2,4-, 2,5-, 2,6-, 3,4- and 3,5-dichlorophenyl, etc., phenyls substituted with an alkyl of 1–6 carbon atoms such as o-, m- and p-methylphenyl, o-, m- and p-ethylphenyl, o-, m- and p-butylphenyl, 2,3-, 2,4-, 2,5-, 2,6-, 3,4- and 3,5-dimethylphenyl, etc., phenyls substituted with an alkoxy of 1–6 carbon atoms such as o-, m- and p-methoxyphenyl, o-, m- and p-ethoxyphenyl, o-, m- and p-propoxyphenyl, etc., phenyls substituted with benzyloxy such as o-, m- and p-benzyloxyphenyl, 2-benzyloxy-3-methylphenyl, 2-benzyloxy-4-methylphenyl, 2-benzyloxy-5-methylphenyl, 2-benzyloxy-5-t-butylphenyl, 2-benzyloxy-3-methoxyphenyl, 2-benzyloxy-4-methoxyphenyl, 2-benzyloxy-5-methoxyphenyl, 2-benzyloxy-3,5-dichlorophenyl, etc., o-, m- and p-cyanophenyl, 2-, 3-, and 4-pyridyl, aryl groups of 5–17 carbon atoms such as α- and μ-naphthyl, etc., alkyl groups of 1–8 carbon atoms, e.g., lower alkyls such as methyl, ethyl, propyl, butyl, pentyl, cyclopentyl, hexyl, cyclohexyl, heptyl, octyl, etc. and haloalkyls such as chloromethyl, dichloromethyl, trichloromethyl, tribromomethyl, trifluoromethyl, 2-chloroethyl, 3-chloropropyl, 4-chlorobutyl, etc. and aralkyl groups of 7-12 carbon atoms such as benzyl, o-, m- and p-tolylmethyl, o-, m- and p-ethylbenzyl, o-, m- and p-methoxybenzyl, o-, m- and p-ethoxybenzyl, 2,3-, 2,4-, 2,5-, 2,6-, 3,4- and 3,5-dimethylbenzyl, 3-sulfamoyl-4-methoxybenzyl, (2,3-, 2,4-, 2,5- and 2,6-dimethoxyphenyl)ethyl, 2-phenylethyl, 2-(o-, m- and p-tolyl)-ethyl, (2,3-, 2,4-, 2,5-, 2,6-, 3,4- and 3,5-dimethylphenyl)ethyl, 3-phenylpropyl, naphthylmethyl, etc.

Examples of representative oxime derivatives include o-methyl, o-octyl, o-cyclohexyl, o-benzyl, o-trimethylsilyl and like oxime derivatives of acetophenone, propiophenone, butyrophenone, isobutyrophenone, chloromethyl(phenyl) ketone, bromomethyl(phenyl) ketone, 2-acetylpyridine, o-methoxyacetophenone, o-ethoxyacetophenone, o-propoxyacetophenone, o-benzyloxyacetopphenone, $\alpha$-acetonaphthone, $\beta$-acetonaphthone, (p-chlorophenyl)methyl ketone, (p-bromophenyl)methyl ketone, (p-cyanophenyl)methyl ketone, 3-sulfamoyl-4-methoxybenzyl methyl ketone, phenyl benzyl ketone, phenyl (o-tolylmethyl) ketone, phenyl (m-tolylmethyl) ketone, phenyl (p-tolylmethyl) ketone, phenyl (2-phenylethyl) ketone, 2-butanone, 2-pentanone, 2-hexanone, 2-heptanone, 2-octanone, 3-heptanone, 3-octanone, 2-decanone, cyclohexyl methyl ketone, cyclohexyl ethyl ketone, cyclohexyl benzyl ketone, o-phenylacetone, (2-phenylethyl) methyl ketone, (2-phenylethyl) ethyl ketone, (3-phenylpropyl) methyl ketone, deoxyanisoin, pinacolone, etc. The syn-isomer or the anti-isomer of these derivatives or mixtures rich in either one of the two isomers are used.

The oxime derivative can be prepared from the corresponding ketone by known methods. When either one of the syn-isomer and the anti-isomer is used, the other isomer remaining after separation can be subjected to syn-anti isomerization to be converted into the required isomers, permitting more effective utilization of the raw material.

As examples of the solvent used in carrying out the reduction, there may be mentioned ethers, sulfides, the mixtures thereof, and the mixtures thereof with hydrocarbon solvents, similar to those used in preparation of the reducing agent. The amount of the solvent used is usually 2 to 50 times the weight of the oxime derivative.

The amount of the reducing agent used is usually 0.2 to 5 times by mole, preferably 0.3 to 2.5 times by mole, in terms of the optically active amine derivative relative to the oxime derivative. When calculated in terms of borane it is usually 1 to 5 times by mole, 2 to 3 times by mole being sufficient to conduct the reaction.

The reduction can be conducted more efficiently in the presence of a Lewis acid. Examples of the Lewis acid include zinc chloride, boron trifluoride, aluminum chloride, aluminum bromide, titanium tetrachloride, tin tetrachloride, tin dichloride, etc. They are used in an amount of usually 0.2 to 1.3 moles per mole of the oxime derivative.

The reduction is carried out usually at 150° C. or below, preferably at −20° to 100° C., but, if necessary, more elevated temperatures can be used.

The progress of the reaction can be confirmed by such means of analysis as gas chromatography, etc.

After completion of the reaction, the reducing agent is deactivated, for example, by addition of a mineral acid such as hydrochloric acid, etc. to the reaction mixture. Subsequently, when the asymmetric auxiliary is an optically active amine having a substituent of the formula (II) as $R_3$, the reaction mixture is, for example, made alkaline and extracted with a solvent such as toluene to obtain the intended optically active amine and said asymmetric auxiliary from the organic layer. Then, the intended product and the asymmetric auxiliary are respectively isolated and recovered by conventional means of separation such as distillation, etc. In the above extraction, when such solvents as hexane and toluene are used, the intended product can be isolated and recovered from the organic layer and the asymmetric auxiliary from the aqueous layer by making use of the solubility difference between the product and the auxiliary. On the other hand, when the asymmetric auxiliary is an optically active amine having hydroxyphenyl as $R_3$, after deactivation of the reductant the reaction mixture may be made alkaline with aqueous sodium hydroxide solution or such and extracted with an organic solvent. Then the intended product can be isolated and recovered from the organic layer, and said ligand can be isolated and recovered by neutralization of the aqueous layer.

The intended optically active amine thus obtained can be further purified by conventional means of purification, e.g., distillation, column chromatography, etc.

The intended optically active amine can be produced in the manner described above. According to the process of the present invention, metal borohydrides which are easy to handle and inexpensive can be used and moreover the yield of the intended product can be improved and the amount of metal borohydride to be used can be reduced. Thus, the process is of great advantage as an industrial method for producing optically active amines.

The present invention will be described in more detail below with reference to Examples, but the invention is not limited thereto.

EXAMPLE 1

Under nitrogen atmosphere at room temperature, 6 mmoles (0.229 g) of sodium borohydride were suspended into a solution consisting of 2.6 mmoles (0.393 g) of (−)-norephedrine and 1.1 g of tetrahydrofuran (THF). Then a solution consisting of 3 mmoles (0.303 g) of 97% sulfuric acid and 0.36 g of THF was added to the suspension at room temperature.

Then, a solution consisting of 2 mmoles (0.479 g) of anti-phenyl (p-tolylmethyl) ketone (o-methyloxime) and 2.8 g of toluene was added and the resulting mixture was stirred at 35° C. for 14 hours and then refluxed for 10 hours.

Thereafter the reaction mixture was cooled down to room temperature, 10 g of 10% hydrochloric acid was added thereto, and the resulting reaction mixture was stirred at the same temperature for 1 hour and then concentrated under reduced pressure. The concentrated product was made alkaline by addition of aqueous sodium hydroxide solution, extracted with hexane and separated into two layers. The hexane layer was concentrated to obtain 0.41 g of 1-phenyl-2-(p-tolyl)ethylamine.

Analysis by gas chromatography revealed that the conversion was 100% and the product had a composition of 100% of amine compound.

The enantiomer ratio of the amine compound was determined by high performance liquid chromatography using an optically active column and found to be 7.7% of R isomer and 92.3% of S isomer.

EXAMPLE 2

The same procedures as in Example 1 were followed except for using 4 g of 1,2-dichloroethane in place of toluene.

Resultantly, the conversion was 100% and the composition was 100% of amine compound. The enantiomer ratio was 7.4% of R isomer and 92.6% of S isomer.

EXAMPLE 3

The same procedures as in Example 1 were followed except for using 2.6 mmoles (0.357 g) of (−)-1-(2-hydroxyphenyl)ethylamine in place of (−)norephedrine.

The conversion was 85.8% and the product had a composition of 99.8% of amine compound and 0.2% of N-methoxy compound (compound in which the C=N double bond alone had been reduced). The enantiomer ratio of the amine compound was 16.8% of R isomer and 83.2% of S isomer.

EXAMPLE 4

Under nitrogen atmosphere, 4.4 mmoles (0.1665 g) of sodium borohydride were suspended into a solution consisting of 2 mmoles (0.302 g) of (−)-norephedrine and 1.1 g of THF. Then a solution consisting of 2.2 mmoles (0.216 g) of 100% sulfuric acid and 0.36 g of THF was added to the suspension at 10° C.

The resulting mixture was stirred at the same temperature for 1 hour, then warmed to 50° C., a solution consisting of 2 mmoles (0.479 g) of anti-phenyl (p-tolylmethyl) ketone (o-methyloxime) and 2.8 g of toluene was added thereto, and the mixture was stirred at the same temperature for 24 hours and further at 80° C. for 24 hours. Subsequent treatments were conducted in the same manner as in Example 1.

The conversion was 99.5%, amine compound 98.6% and N-methoxy compound 1.4%. The enantiomer ratio of the amine compound was 7.1% of R isomer and 92.9% of S isomer.

EXAMPLE 5

The same procedures as in Example 4 were followed except for using 2 mmoles (0.4225 g) of (−)-1-(2,5-dimethoxyphenyl)-2-amino-1-propanol in place of (−)-norephedrine.

The conversion was 97.1%, amine compound 63.6% and N-methoxy compound 36.4%. The enantiomer ratio of the amine compound was 6.7% of R isomer and 93.3% of S isomer.

EXAMPLE 6

The same procedures as in Example 4 were followed except for using 4 mmoles (0.1513 g) of sodium borohydride and 2 mmoles (0.1961 g) of 100% sulfuric acid.

The conversion was 87.9% and the product had a composition of 80.5% of amine compound and 19.5% of N-methoxy compound. The enantiomer ratio of the amine compound was 4.6% of R isomer and 95.4% of S isomer.

EXAMPLE 7

The same procedures as in Example 4 were followed except for using 4 mmoles (0.1513 g) of sodium borohydride and 2 mmoles (0.1961 g) of 100% sulfuric acid and using a mixture consisting of 2.8 g of toluene and 2 mmoles (0.2839 g) of boron trifluoride-ether complex in place of toluene.

The conversion was 97.6% and the product had a composition of 95.7% of amine compound and 4.3% of N-methoxy compound. The enantiomer ratio of the amine compound was 11.7% of R isomer and 88.3% of S isomer.

EXAMPLE 8

The same procedures as in Example 4 were followed except for using 4 mmoles (0.1513 g) of sodium borohydride and 2 mmoles (0.1961 g) of 100% sulfuric acid and using a mixture consisting of 2.8 g of toluene and 1 mmole (0.1363 g) of zinc chloride in place of toluene.

The conversion was 92.8% and the composition was 100% of amine compound. The enantiomer ratio was 7.5% of R isomer and 92.5% of S isomer.

EXAMPLE 9

The same procedures as in Example 4 were followed except for using 2 mmoles (0.227 g) of 95% sulfuric acid in place of 100% sulfuric acid.

The conversion was 87.9% and the product had a composition of 80.3% of amine compound and 19.7% of N-methoxy compound. The enantiomer ratio of the amine compound was 6.1% of R isomer and 93.9% of S isomer.

EXAMPLE 10

The same procedures as in Example 4 were followed except for using 2 mmoles (0.359 g) of (+)-2-amino-1-(2,4-dimethylphenyl)-1-propanol in place of (−)-norephedrine.

The conversion was 89.6% and the product had a composition of 79.5% of amine compound and 20.5% of N-methoxy compound. The enantiomer ratio of the amine compound was 81.8% of R isomer and 18.2% of S isomer.

EXAMPLE 11

The same procedures as in Example 4 were followed except for using 2 mmoles (0.427 g) of (1S,2R)-2-amino-1,2-diphenyl-1-ethanol in place of (−)-norephedrine.

The conversion was 35.8% and the product had a composition of 42.5% of amine compound and 57.5% of N-methoxy compound. The enantiomer ratio of the amine compound was 19.1% of R isomer and 80.9% of S isomer.

EXAMPLE 12

The same procedures as in Example 4 were followed except for using 2 mmoles (0.274 g) of (R)-(−)-2-phenylglycinol in place of (−)-norephedrine.

The conversion was 98.6% and the product had a composition of 95.5% of amine compound and 4.5% of N-methoxy compound. The enantiomer ratio of the amine compound was 92.5% of R isomer and 7.5% of S isomer.

EXAMPLE 13

The same procedures as in Example 4 were followed except for using 2 mmoles (0.206 g) of (R)-(−)-2-amino-3-methyl-1-butanol in place of (−)-norephedrine.

The conversion was 99.7% and the product had a composition of 97.9% of amine compound and 2.1% of N-methoxy compound. The enantiomer ratio of the amine compound was 94% of R isomer and 6% of S isomer.

EXAMPLE 14

The same procedures as in Example 4 were followed except for using 2 mmoles (0.455 g) of (S)-2-amino-1,1-diphenyl-1-propanol in place of (−)-norephedrine.

The conversion was 48.1% and the product had a composition of 43.9% of amine compound and 56.1% of N-methoxy compound. The enantiomer ratio of the amine compound was 26.4% of R isomer and 73.6% of S isomer.

EXAMPLE 15

The same procedures as in Example 4 were followed except for using 2 mmoles (0.298 g) of antiacetophenone o-methyloxime in place of anti-phenyl (p-tolylmethyl) ketone (o-methyloxime).

The conversion was 91.7% and the product had a composition of 61.9% of amine compound and 38.1% of N-methoxy compound. The enantiomer ratio of the amine compound was 5.3% of R isomer and 94.7% of S isomer.

EXAMPLE 16

The same procedures as in Example 4 were followed except for using 2 mmoles (0.343 g) of (S)-(−)-(1-naphthyl)ethylamine in place of (−)-norephedrine and using 4 mmoles (0.1513 g) of sodium borohydride.

The conversion was 100% and the product had a composition of 100% of amine compound The enantiomer ratio of the amine compound was 31% of R isomer and 69% of S isomer.

EXAMPLE 17

The same procedures as in Example 4 were followed except for using 2 mmoles (0.571 g) of antideoxyanisoin oxime o-methyl ether in place of antiphenyl (p-tolylmethyl) ketone (o-methyloxime).

The conversion was 92.8% and the product had a composition of 98.7% of amine compound and 1.3% of N-methoxy compound. The enantiomer ratio of the amine compound was 11.1% of R isomer and 88.9% of S isomer.

EXAMPLE 18

Under nitrogen atmosphere at room temperature, 4.4 mmoles (0.1665 g) of sodium borohydride were suspended into a solution consisting of 2 mmoles (0.302 g) of (S)-(−)-2-amino-3-phenyl-1-propanol and 1.1 g of THF. Then a solution consisting of 2.2 mmoles (0.222 g) of 97% sulfuric acid and 0.36 g of THF was added to the suspension at 10° C.

The resulting mixture was stirred at the same temperature for 1 hour, then warmed to 50° C., a solution consisting of 2 mmoles (0.479 g) of anti-phenyl (p-tolylmethyl) ketone (o-methyloxime) and 2.8 g of toluene was added thereto, and the mixture was stirred at the same temperature for 8 hours and further at 80° C. for 8 hours. Subsequent treatments were conducted in the same manner as in Example 1.

The conversion was 92.9%, and the product had a composition of 85.8% of amine compound and 14.2% of N-methoxy compound. The enantiomer ratio of the amine compound was 10.9% of R isomer and 89.1% of S isomer.

EXAMPLE 19

The same procedures as in Example 4 were followed except for using 2 mmoles (0.274 g) of (R)-(−)-2-phenylglycinol in place of (−)-norephedrine, and 2 mmoles (0.298 g) of anti-acetophenone o-methyloxime in place of anti-phenyl (p-tolylmethyl) ketone (o-methyloxime).

The conversion was 97.0% and the product had a composition of 78.1% of amine compound and 21.9% of N-methoxy compound. The enantiomer ratio of the amine compound was 88.9% of R isomer and 11.1% of S isomer.

COMPARATIVE EXAMPLE 1

The same procedures as in Example 4 were followed except for using 1.46 mmoles (0.146 g) of 99% phosphoric acid in place of 100% sulfuric acid.

The conversion was 31.1% and the product had a composition of 26% of amine compound and 74% of N-methoxy compound. The enantiomer ratio of the amine compound was 9% of R isomer and 91% of S isomer.

COMPARATIVE EXAMPLE 2

The same procedures as in Example 4 were followed except for using 2.2 mmoles (0.3122 g) of boron trifluoride-ether complex in place of 100% sulfuric acid.

The conversion was 64.7% and the product had a composition of 100% of amine compound. The enantiomer ratio was 15.2% of R isomer and 84.8% of S isomer.

What is claimed is:

1. A process for producing an optically active amine represented by the formula (IV)

$$H_2N-\overset{*}{C}H\diagup_{R_8}^{R_7} \quad (IV)$$

wherein $R_7$ and $R_8$ each denote an alkyl group, aryl group or aralkyl group, providing that they do not denote the same group at the same time, and * indicates an asymmetric carbon atom, which comprises reacting an asymmetric reducing agent obtained from (1) an optically active amine derivative represented by the formula (I)

$$R_1-\overset{*}{\underset{NHR_2}{C}H}-R_3 \quad (I)$$

wherein $R_1$ denotes an alkyl group, aryl group, or aralkyl group; $R_2$ denotes a hydrogen atom, alkyl group or aralkyl group; $R_3$ denotes an aryl group or a substituent represented by the formula (II)

$$-\underset{R_5}{\overset{R_4}{\underset{|}{\overset{|}{C}}}}-OH \quad (II)$$

wherein $R_4$ and $R_5$ each denote a hydrogen atom, aryl group or aralkyl group, and * is as defined above, (2) a metal borohydride and (3) sulfuric acid, with either the syn-isomer or the anti-isomer of an oxime derivative represented by the formula (III) or with a mixture rich in either one of the two isomers

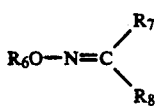

wherein $R_6$ denotes an alkyl group, aralkyl group or alkyl-substituted silyl group, and $R_7$ and $R_8$ are as defined above.

2. A process according to claim 1, wherein the metal borohydride is lithium borohydride, sodium borohydride, potassium borohydride or zinc borohydride.

3. A process according to claim 1, wherein the metal borohydride is used in an amount of 0.8 to 8 times by mole in terms of borane relative to the optically active amine derivative (I).

4. A process according to claim 1, wherein sulfuric acid is used in an amount of 0.7 to 1.3 equivalents relative to the metal borohydride.

5. A process according to claim 1, wherein the asymmetric reducing agent is used in an amount of 0.2 to 5 times by mole in terms of the optically active amine derivative (I) relative to the oxime derivative (III).

6. A process according to claim 1, wherein the asymmetric reducing agent is used in an amount of 1 to 5 times by mole in terms of borane.

7. A process according to claim 1, wherein the asymmetric reduction is conducted in the presence of a Lewis acid.

8. A process according to claim 7, wherein the Lewis acid is zinc chloride, boron trifluoride, aluminum chloride, aluminum bromide, titanium tetrachloride, tin tetrachloride or tin dichloride.

9. A process according to claim 7, wherein the Lewis acid is used in an amount of 0.2 to 1.3 times by mole relative to the oxime derivative (III).

10. A process according to claim 1, wherein $R_1$ in the optically active amine derivative (I) is an alkyl group of 1 to 6 carbon atoms, phenyl group, or aralkyl group of 7 to 12 carbon atoms.

11. A process according to claim 1, wherein $R_2$ in the optically active amine derivative (I) is a hydrogen atom, alkyl group of 1 to 6 carbon atoms or aralkyl group of 7 to 12 carbon atoms.

12. A process according to claim 1, wherein $R_3$ in the optically active amine derivative (I) is a substituent represented by the formula (II)

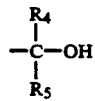

wherein $R_4$ and $R_5$ are each a hydrogen atom, aryl group, alkyl group or aralkyl group.

13. A process according to claim 12, wherein $R_4$ and $R_5$ are each a hydrogen atom, phenyl group optionally substituted with an alkyl of 1 to 6 carbon atoms and/or an alkoxy of 1 to 6 carbon atoms, or aralkyl group of 7 to 12 carbon atoms.

14. A process according to claim 1, wherein the optically active amine derivative (I) is optically active norephedrine, 1-(2,5-dimethoxy-phenyl)-2-amino-1-propanol, 2-amino-1-(2,4-dimethylphenyl)-1-propanol or 2-amino-1,2-diphenyl-1-ethanol.

15. A process according to claim 1, wherein the optically active amine derivative (I) is optically active 2-phenylglycinol, 2-amino-3-methyl-1-butanol, 2-amino-1,1-diphenyl-1-propanol or 2-amino-3-phenyl-1-propanol.

16. A process according to claim 1, wherein $R_3$ in the optically active amine derivative (I) is a phenyl group, alkyl group of 1 to 6 carbon atoms, hydroxyphenyl group optionally substituted with an alkyl of 1 to 6 carbon atoms or an alkoxy of 1 to 6 carbon atoms, or aryl group selected from 1-naphthyl and 2-naphthyl.

17. A process according to claim 1, wherein the optically active amine derivative (I) is optically active 1-(2-hydroxyphenyl)ethylamine or 1-(1-naphthyl)ethylamine.

18. A process according to claim 1, wherein $R_6$ in the oxime derivative (III) is an alkyl group of 1 to 10 carbon atoms, aralkyl group of 7 to 12 carbon atoms, or alkylsilyl group of 3 to 12 carbon atoms.

19. A process according to claim 1, wherein $R_7$ and $R_8$ in the oxime derivative (III) are each an aryl group of 5 to 17 carbon atoms, alkyl group of 1 to 8 carbon atoms, or aralkyl group of 7 to 12 carbon atoms.

20. A process according to claim 19, wherein the aryl group of 5 to 17 carbon atoms is an unsubstituted phenyl group, halogen-substituted phenyl group, $(C_1-C_6)$alkyl-substituted phenyl group, $(C_1-C_6)$alkoxy-substituted phenyl group, benzyloxy-substituted phenyl group, cyanophenyl group, pyridyl group, or naphthyl group.

21. A process according to claim 19, wherein the aralkyl group of 7 to 12 carbon atoms is benzyl, o-, m- or p-tolylmethyl, o-, m- or p-ethylbenzyl, o-, m- or p-methoxybenzyl, o-, m- or p-ethoxybenzyl, 2,3-, 2,4-, 2,5-, 2,6-, 3,4- or 3,5-dimethylbenzyl, 3-sulfamoyl-4-methoxybenzyl, (2,3-, 2,4-, 2,5- or 2,6-dimethoxyphenyl)ethyl, 2-phenylethyl, 2-(o-, m- or p-tolyl)ethyl, (2,3-, 2,4-, 2,5-, 2,6-, 3,4- or 3,5-dimethylphenyl)-ethyl, 3-phenylpropyl or naphthylmethyl.

22. A process according to claim 1, wherein the oxime derivative (III) is phenyl (p-tolymethyl) ketone (o-methyloxime) or deoxyanisoin oxime o-methyl ether.

* * * * *